(12) United States Patent
Wallach et al.

(10) Patent No.: US 6,262,239 B1
(45) Date of Patent: *Jul. 17, 2001

(54) TNF RECEPTOR-SPECIFIC ANTIBODIES

(75) Inventors: David Wallach, Rehovot (IL); Jacek Bigda, Gdansk (PL); Igor Beletsky, Pushino (RU); Igor Mett, Rehovot (IL); Hartmut Engelmann, Munich (DE)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 08/476,862

(22) Filed: Jun. 7, 1995

(30) Foreign Application Priority Data

| May 18, 1989 | (IL) | 90339 |
| Aug. 6, 1989 | (IL) | 91229 |
| Apr. 6, 1990 | (IL) | 94039 |
| Oct. 12, 1993 | (IL) | 107267 |

(51) Int. Cl.$^7$ ............................. C07K 16/28; C12N 5/12
(52) U.S. Cl. ................................. 530/388.22; 530/387.1; 530/387.9; 530/388.1; 530/388.2; 435/326; 435/331; 435/332; 435/334; 435/346
(58) Field of Search ........................... 424/133.1, 139.1, 424/141.1, 144.1, 152.1, 130.1; 514/2; 530/388.7, 387.9, 388.22, 388.85, 391.1, 387.1; 435/326, 334

(56) References Cited

U.S. PATENT DOCUMENTS

| 4,677,063 | 6/1987 | Mark et al. . |
| 4,898,818 | 2/1990 | Nakai et al. . |
| 4,948,875 | 8/1990 | Tanaka et al. . |
| 4,990,455 | 2/1991 | Yamagishi et al. . |
| 5,344,915 | 9/1994 | LeMaire . |

FOREIGN PATENT DOCUMENTS

| 58769/90 | 1/1991 | (AU) . |
| 0 334 185 A2 | * 9/1989 | (EP) . |
| 0398327 | 11/1990 | (EP) . |
| 0418014 | 3/1991 | (EP) . |
| 0648783 | * 4/1995 | (EP) . |
| 90/13575 | 11/1990 | (WO) . |

OTHER PUBLICATIONS

Brockhaus et al. PNAS 87:3127, Apr., 1990.*
Loetsher et al. J. Biol. Chem. 265: 20131, Nov. 1990.*
Corrcorran et al. Eur. J. Biochem 223: 831, 1994.*
Balavoine et al, "Prostaglandin E$_2$ and Collagenase Production by Fibroblasts and Synovial Cells Is Regulated by Urine–derived Human Interleukin 1 and Inhibitor(s)", *J. Clin. Invest.*, 78:1120–1124 (1986).
Beutler et al, "Passive Immunization Against Cachectin/Tumor Necrosis Factor Protects Mice from Lethal Effect of Endotoxin", *Science*, 229:869–871 (1985).
Beutler et al, "Cachectin: More Than a Tumor Necrosis Factor", *New Eng. J. Med.*, 316(7):379–385 (1987).
Beutler et al, *Tumor Necrosis Factors . . .* , Raven Press, New York, pp. 145 and 383 (1992).
Bigda et al, "Dual Role of the p75 Tumor Necrosis Factor (TNF) Receptor in TNF Cytotoxicity", *J. Exp. Med.*, 180:445–460 (1994).
Brockhaus et al, "Monoclonal Antibodies Against the TNF–Receptor Inhibit . . . ," 2nd Int'l Conf. Tumor Necrosis Factor and Related Cytokines, Jan. 15–20, 1989, p. 140.
Chen et al, "Mapping the domain(s) critical for the binding of human tumor necrosis factor alpha to its two receptors", *J. Biol. Chem.*, 270(6):2874–8 (1995) (abstract).
Creasey et al, "Biological Effects of Recombinant Human Tumor Necrosis Factor and Its Novel Muteins on Tumor and Normal Cell Lines", *Cancer Research*, 47:145–149 (1987).
Engelmann et al, "Two Tumor Necrosis Factor–binding Proteins Purified from Human Urine", *J. Biol. Chem.*, 265(3):1531–1536 (1990).
Harris et al, "Therapeutic antibodies—the coming of age", *Tibtech*, 11:42–44 (1993).
Hohmann et al, Two Different Cell Types Have Different Major Receptors for Human Tumor Necrosis Factor (TNFalpha), *J. Biol. Chem.*, 264(25)14927–14934 (1989).
Hohmann et al, "Two Different Cell Types Have Different Major Receptors for . . . ", 2nd Int'l Conf. Tumor Necrosis Factor and Related Cytokines, Jan. 15–1/20, 1989, p. 143.
Natanson et al, "Selected Treatment Strategies for Septic Shock Based on Proposed Mechanisms of Pathogenesis", *Annals of Int. Med.*, 120(9):771–783 (1994).
Parrillo, J.E., "Pathogenetic Mechanism of Septic Shock", *New Eng. J. of Med.*, 328(20):1471–1477 (1993).
Peetre et al, "A tumor necrosis factor binding protein is present in human biological fluids", *Eur. J. Haematol.*, 41:414–419 (1988).
Schall et al, "Molecular Cloning and Expression of a Receptor for Human Tumor Necrosis Factor", *Cell*, 61:361–370 (1990).
Seckinger et al, "A Human Inhibitor of Tumor Necrosis Factor alpha", *J. Exp. Med.*, 167:1511–1516 (1988).
Smith et al, "A Receptor for Tumor Necrosis Factor Defines an Unusual Family of Cellular and Viral Proteins", *Science*, 248:1019–1023 (1990).
Stauber et al, "Human Tumor Necrosis Factor–alpha Receptor", *J. Biol. Chem.*, 263(35):19098–19104 (1986).

(List continued on next page.)

Primary Examiner—Phillip Gambel
(74) *Attorney, Agent, or Firm*—Browdy and Neimark

(57) ABSTRACT

Antibodies to Tumor Necrosis Factor receptors (TNF-Rs) which inhibit the cytocidal effect of TNF but not its binding to the TNF-Rs, and ligands interacting with other receptors of the TNF/NGF family, are provided together with methods of producing them. The antibodies preferably bind to the fourth cysteine rich domain of the p75 TNF receptor or to the region between said fourth cysteine rich domain and the cell membrane.

5 Claims, 9 Drawing Sheets

OTHER PUBLICATIONS

Tracey et al, "Shock and Tissue Injury Induced by Recombinant Human Cachectin," *Science*, 234:470–474 (1986).

Tracey et al, "Anti–cachectin/TNF monoclonal antibodies prevent septic shock during lethal bacteraemia", *Nature*, 330:662–664 (1987).

Unglaub et al, "Downregulation of Tumor Necrosis Factor (TNF) Sensitivity Via Modulation of TNF Binding Capacity by Protein Kinase C Activators", *J. Exp. Med.*, 166:1788–1797 (1987).

Wallach, D., "Cytotoxins (Tumor Necrosis Factor, Lymphotoxin and Others); Molecular Functional Characteristics . . . ", *Interferon 7*, pp. 90–124, Jul. 1986.

Whitlow et al, "Single–Chain Fv Proteins and Their Fusion Proteins", *Methods*, 2(2):97–105 (1991).

\* cited by examiner

FIG. 2A

```
1   gcgagcgcag cggagcctgg agagaaggcg ctgggctgcg agggcgcgag gcgcgaggg caggggcaa ccggaccccg
81  cccgcaccc atg gcg ccc gtc gcc gcg ctg gcc gtc gga ctg gag ctc tgg gct gcg
           Met Ala Pro Val Ala Ala Leu Ala Val Gly Leu Glu Leu Trp Ala Ala
           -22
147 gcg cac gcc ttg ccc gcc cag gtg gca ttt aca ccc tac gcc ccg gag ccc ggg agc aca tgc cgg
    Ala His Ala Leu Pro Ala Gln Val Ala Phe Thr Pro Tyr Ala Pro Glu Pro Gly Ser Thr Cys Arg
    -1 +1                                  10
213 ctc aga gaa tac tat gac cag aca gct cag atg tgc tgc agc atg tgc caa cat gca
    Leu Arg Glu Tyr Tyr Asp Gln Thr Ala Gln Met Cys Cys Ser Lys Cys Ser Pro Gly Gln His Ala
    279                                     32
    aaa gtc ttc tgt acc aag acc tcg gac acc gtg tgt gac tcc tgt gag gac agc tac acc cag
    Lys Val Phe Cys Thr Lys Thr Ser Asp Thr Val Cys Asp Ser Cys Glu Asp Ser Thr Tyr Thr Gln
    345                                     54
    ctc tgg aac tgg gtt ccc gag tgc ttg agc tgc ggc tcc cgc tgt agc tct gac cag gtg gaa act
    Leu Trp Asn Trp Val Pro Glu Cys Leu Ser Cys Gly Ser Arg Cys Ser Ser Asp Gln Val Glu Thr
    411                                     76
    caa gcc act cgg gaa cag aad cgc atc tgc acc tgc agg ccc ggc tac tgc gcg ctg agc
    Gln Ala Cys Thr Arg Glu Gln Asn Arg Ile Cys Thr Cys Arg Pro Gly Trp Tyr Cys Ala Leu Ser
    477                                     98
    aag cag gag ggg tgc cgg ctg tgc gcg ccg ctg ccc aag tgc cgc ccg ggc ttc ggc gtg gcc aga
    Lys Gln Glu Gly Cys Arg Leu Cys Ala Pro Leu Pro Lys Cys Arg Pro Gly Phe Gly Val Ala Arg
    543                                     120
    cca gga act gaa aca tca gac gtg gtg tgc aag ccc tgt gcc ccc ggg acg ttc tcc aac acg act
    Pro Gly Thr Glu Thr Ser Asp Val Val Cys Lys Pro Cys Ala Pro Gly Thr Phe Ser Asn Thr Thr
    609                                     142
    tca tcc acg gat att tgc agg ccc cac cag atc tgt aac gtg gcc ata ccc ggg aat gca agc
    Ser Ser Thr Asp Ile Cys Arg Pro His Gln Ile Cys Asn Val Ala Ile Pro Gly Asn Ala Ser
    675                                     164
    atg gat gca gtc tgc acg tcc ccc acc cgg agt atg ccg gga gca gta cac tta ccc
    Met Asp Ala Val Cys Thr Ser Pro Thr Arg Ser Met Ala Pro Gly Ala Val His Leu Pro
    741                           166
```

TBPII

FIG.2B

```
cag cca gtg tcc aca cga tcc caa cac cag acg act cca gaa ccc agc act gct cca agc acc
Gln Pro Val Ser Thr Arg Ser Gln His Thr Gln Pro Glu Pro Thr Ala Pro Ser Thr
807                                                                      208 tcc ttc ctg ctc cca atg ggc ctc ccc agc ccc cca gct gaa ggg agc act ggc gac
Ser Phe Leu Pro Met Gly Pro Ser Pro Pro Ala Glu Gly Ser Thr Gly Asp
873                                                    230

TRANSMEMBRANE
gtt gga ctg att gtg ggt gtg aca gcc ttg gtt cta ata gga gtg gtg aac tgt gtc atc
Val Gly Leu Ile Val Gly Val Thr Ala Leu Val Leu Ile Ile Gly Val Val Asn Cys Val Ile
939                                                252

DOMAIN
atg acc cag gtg aaa aag aag ccc ctg tgc ctg cag aga gaa gcc aag gtg cct ttg cct gcc
Met Thr Gln Val Lys Lys Lys Pro Leu Cys Leu Gln Arg Glu Ala Lys Val Pro His Leu Pro Ala
1005                                    274 gat aag gcc cgg ggt aca cag ggc ccc gag cag cag cac ctg atc aca gcg ccg agc tcc agc
Asp Lys Ala Arg Gly Thr Gln Gly Pro Glu Gln Gln His Leu Ile-Thr Ala Pro Ser Ser Ser
1071                                                            296 agc agc tcc ctg gag tcc agt gcg gcc aga agg gcg ccc act cgg acc cag aac cag cca cag
Ser Ser Ser Leu Glu Ser Ser Ala Ala Arg Arg Ala Pro Thr Arg Thr Asn Gln Pro Gln
1137                                                                318 gca cca ggc gtg gag gcc agt ggg gcg gag gcc cgg gcc agc acc ggg agc tca gat tct tcc
Gly Ala Gly Val Glu Ala Ser Gly Ala Glu Ala Arg Asp Ser Arg Gly Ser Ser Ser Asp Ser
1203                                                        340 ctt ggt ggc cat ggg acc tcc caa gtc aat gtc acc gtc aac gtg tgt agc ccc tcg gag tcc
Leu Gly Gly His Gly Thr Ser Gln Val Asn Val Thr Val Asn Val Cys Ser Pro Ser Glu Ser
1269                                                    362 agc tca cag tgc tcc tcc tcc caa gcc agc ccc aca atg gga gac aca gat tcc agc ctg gag cac
Ser Ser Gln Cys Ser Ser Ser Gln Ala Ser Pro Thr Met Gly Asp Thr Asp Ser Ser Leu Glu His
1335                                                384 ccg aag gac gag cag gtc ccc ttc tcc aag gag aag tgt ttc cgg gca ttc gcc ctg cag ctg gag acg cca
Pro Lys Asp Glu Gln Val Pro Phe Ser Lys Glu Lys Cys Phe Arg Ala Phe Ser Gln Leu Glu Thr Pro
1401                                                406 gag acc ctg ctg ggg agc acc gaa gag aag agc ccc ctg cct gga gtg cct gat gct ggg atg aag
Glu Thr Leu Leu Gly Ser Thr Glu Glu Lys Ser Pro Leu Pro Gly Val Pro Asp Ala Gly Met Lys
1467                                                428 ccc agt taa ccaggccggt gtgggctgtg tcgtagccaa ggtgggctga gccctggcag gatgaccctg cgaaggggc
Pro Ser End
439
```

FIG. 2C

```
1545
cctggtcctt ccaggccccc accactagga ctctgaggct ctttctgggc caagttcctc tagtgccctc cacagccgca
gcctccctct gacctgcagg ccaagagcag aggcagcgag ttggggaaag ccctgctgc catggtgtgt ccctctcgga
aggctggctg ggcatggacg ttcgggcat gctggggcaa gtccctgact ctctgtgacc tgccccgccc agctgcacct
gccagcctgg cttctggagc cctggtttt tttgtttgtt tgtttgtttgtt tctcccctg ggctctgccc
agctctggct tccagaaac cccagcatcc ttttctgcag aggcttc tggagaggag ggatgctgcc tgagtcaccc
atgaagacag gacagtgctt ctgcctgagg cagagactgc ggggctctg tgtagggagg aggtgcagc
cctgtaggga acggggtcct tcaagttagc tcaggaggct tggaaagcat cacctcaggc caggtgcagt ggctcacgcc
tatgatccca gcactttggg aggctgaggc gggtggatca cctgaggtta ggagttcgag accagcctgg ccaacatggt
aaaacccat ctctactaaa aatacagaaa ttagccgggc ......3683
                                                                      acctcaggc ggctcacgcc
                                                                                2075
```

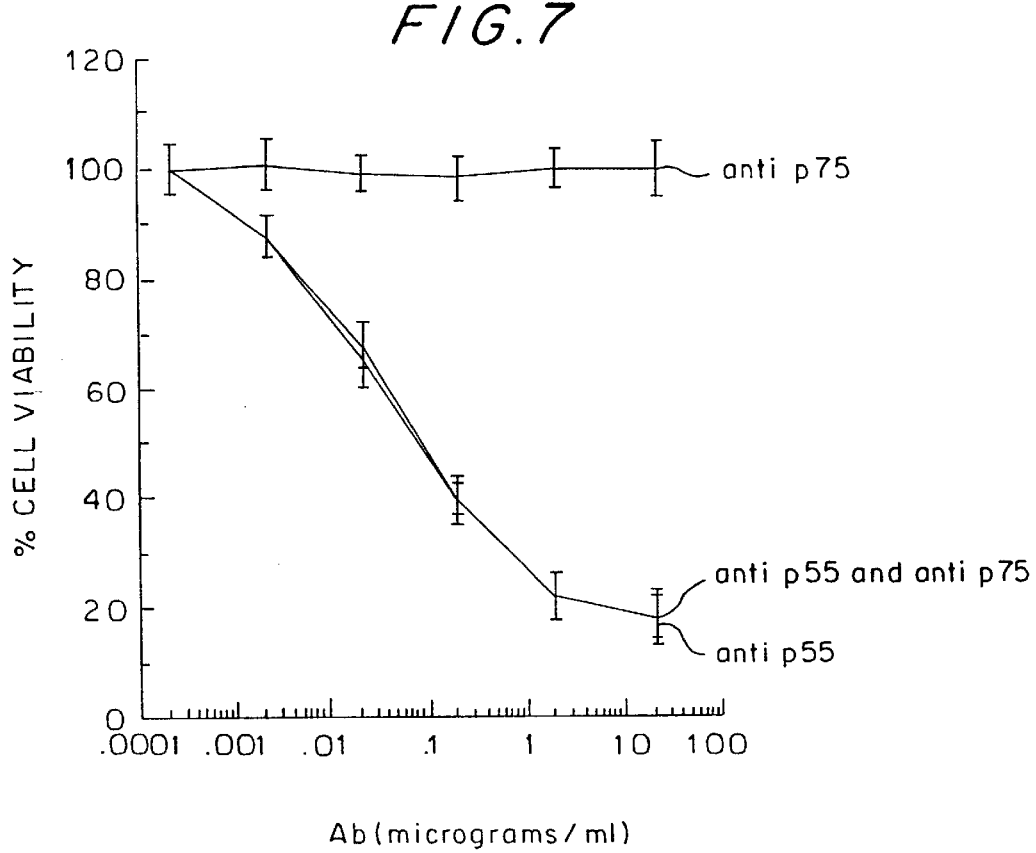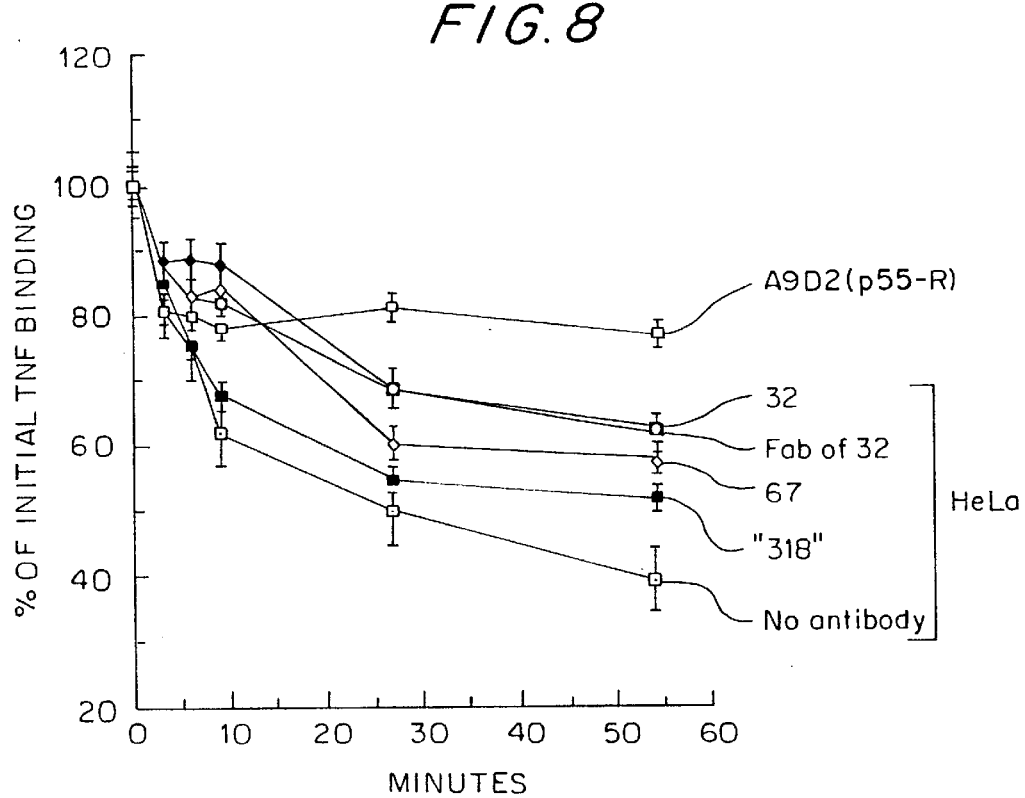

FIG. 9

```
hu p55 TNF-R(3-42)     VCPQGKYIHPQNN----------SICC-TKCHKGTYLYND--CPGPGQDTDCR
hu p75 TNF-R(39-76)    TCRLREYYD-QTA----------QMCC-SKCSPGQHAKVF--CTKTS-DTVCD
hu FAS(31-67)          QNLEGLH-HDGQF----------CH-KPCPPGERKARD----CTVNGDEPDCV
hu NGF-R(3-37)         ACPTGLYTHSGE-----------CC-KACNLGEGVAQP----CGA--NQTVCE
hu CDw40(25-60)        ACREKQYLINSQ-----------CC-SLCQPGQKLVSD----CTEF-TETECL
rat Ox40(25-60)        NCVKDTYPSGHK-----------CC-RECQPGHGMVSR----CDHT-RDTVCH hu p55 TNF-R(43-86)    ECESGSFTASEHHL-RHCLSC--SKCRKENGQVEISSCTVD-RDTVCG
hu p75 TNF-R(77-119)   SCEDSTYTQLWNWV-PECLSCGSRCSDD--QVETQACTRE-QNRICT
hu FAS(68-112)         PCQEGKEYTDKAHFSSKCRRC--RLCDEGHGLEVEINCTRT-QNTKCR
hu NGF-R(38-80)        PCLDSVTSSDVVSATEPCKPC--TECVGLQSHSAP--CVEA-DDAVCR
hu CDw40(61-104)       PCGESEFLDTWHRETN--KYCDPNLGLRVQQKGTSE-TDTICT
rat Ox40(61-104)       PC-EPGEYNEAVNY-DTCKQC-TQCNHRSGSELKQNCTPT-EDTVCQ hu p55 TNF-R(87-126)   -CRKNQYRHYWSENLFQCFNC----SLCLHGT-VHLSCQEK-QNTVC-
hu p75 TNF-R(120-162)  -CRPGWYCA--LSKQEGCRLCAPLRKCRPGFGVARPGTET-SDVVCK
hu FAS(113-149)        -CKPNFFCN--STVCEHCDPC---TKCEHGI-IKE-CTLT-SNTKC-
hu NGF-R(81-119)       -CAYGYYQD--ETTGRCEAC----RVCEAGSGLVFSCQDK-QNTVCE
hu CDw40(105-144)      -CEEGWHC---TSEACESVLHRSCSPGFGVKQIATGV-SDTICE
rat Ox40(105-123)      -CRBGTQP----RQDS-------SHKLGVD--------CV hu p55 TNF-R(127-155)  TCHAGFFLR--ENE-----CVSC-SNCKKSL----ECTK---LC-
hu p75 TNF-R(163-201)  ECAPGTFSNTTSST-DICRPH-QICN-----VVA--IPGNASMDAVCT
hu FAS(120-161)        ECPDGTYSDEAHHV-DPCLPC-TVCEDTERQLR--ECTRW-ADAECE
hu NGF-R(145-186)      ECPVGFFSNVSSAF-EKCHP--TSCETKDLVQ--QAGTNKTDVVCG
hu CDw40(124-164)      PCEPGHFSPGSHQ----ACKPW-TNCTLSGKQIR---HPASNSLDTVCE
```

TNF RECEPTOR-SPECIFIC ANTIBODIES

FIELD OF THE INVENTION

The present invention relates to ligands to Tumor Necrosis Factor receptors (TNF-Rs) which inhibit the effect of TNF but not its binding to the TNF-Rs, as well as to ligands interacting with other receptors of the TNF/NGF family.

BACKGROUND OF THE INVENTION

Tumor necrosis factor (TNF) is a pleiotropic cytokine, produced by a number of cell types, mainly by activated macrophages. It is one of the principal mediators of the immune and inflammatory response. Interest in its function has greatly increased, recently, in view of evidence of the involvement of TNF in the pathogenesis of a wide range of disease states, including endotoxin shock, cerebral malaria and graft-versus-host reaction. Since many of the effects of TNF are deleterious to the organism, it is of great interest to find ways of blocking its action on host cells. An evident target for such intervention are the molecules to which TNF has to bind in order to exert its effects, namely the TNF-Rs. These molecules exist not only in cell-bound, but also in soluble forms, consisting of the cleaved extra-cellular domains of the intact receptors (see Nophar et al., EMBO Journal, 9(10):3269–78, 1990). The soluble receptors maintain the ability to bind TNF, and thus have the ability to block its function by competition with surface receptors.

Another method of TNF inhibition based on the principle of competing with cell-bound molecules, is the use of antibodies recognizing TNF receptors and blocking the ligand binding.

The cell surface TNF-Rs are expressed in almost all cells of the body. The various effects of TNF, the cytotoxic, growth-promoting and others, are all signalled by the TNF receptors upon the binding of TNF to them. Two forms of these receptors, which differ in molecular size: 55 and 75 kilodaltons, have been described, and will be called herein p55 and p75 TNF-R, respectively. It should be noted, however, that there exist publications which refer to these receptors also as p60 and p80.

The TNF-Rs belong to a family of receptors which are involved in other critical biological processes. Examples of these receptors are the low affinity NGF receptor, which plays an important role in the regulation of growth and differentiation of nerve cells. Several other receptors are involved in the regulation of lymphocyte growth, such as CDw40 and some others. Another member of the family is the FAS receptor also called APO, a receptor which is involved in signalling for apoptosis and which, based on a study with mice deficient in its function, seems to play an important role in the etiology of a lupus-like disease. Herein, this family of receptors is called "TNF/NGF receptor family".

One of the most striking features of TNF compared to other cytokines, thought to contribute to the pathogenesis of several diseases, is its ability to elicit cell death. The cell-killing activity of TNF is thought to be induced by the p55 receptor. However, this p55 receptor activity can be assisted by the p75 receptor, through a yet unknown mechanism.

Parent application Ser. No. 07/524,263 and European patent publications 398,327 and 412,486 disclose antibodies to the soluble TNF-Rs. These antibodies were found to recognize the soluble TNF-Rs and to inhibit the binding of TNF to the TNF-Rs on the cell surface. Monovalent F(ab) fragments blocked the effect of TNF, while intact antibodies were observed to mimic the cytotoxic effect of TNF. European patent publication 585,939 describes ligands interacting with a certain region in TNF-Rs.

SUMMARY OF THE INVENTION

The present invention provides a ligand to a member of the TNF/NGF receptor family, which binds either to the region of the fourth cysteine rich domain of such a receptor, or to the region between it and the cell membrane.

The region of the fourth cysteine rich domain will be called herein, for simplicity's sake, the "67 epitope" and the antibodies recognizing it the "group 67" antibodies. This region may extend between about amino acids pro-141 and thr-179 in the p75 TNF-R (residues 163–201 of SEQ ID NO:2) or a corresponding region in another member of the TNF/NGF family. More particularly, the region may extend between about amino acids pro-141 and cys-163 of the p75 TNF-R (residues 163–185 of SEQ ID NO:2) or a corresponding region in another member of the TNF/NGF family. The ligand downstream of the fourth cysteine rich domain includes the amino acid sequence between about thr-179 and about the end of the extracellular domain of the receptor (residues 201–257 of SEQ ID NO:2) or a corresponding region in another member of the TNF/NGF family.

Preferably, the receptor is the TNF-R, in particular the p75 TNF-R.

One such ligand includes the amino acid sequence for the CDR region of the heavy chain of monoclonal antibody no. 67 and/or of the light chain thereof.

Another such ligand includes the amino acid sequence for the CDR region of the heavy chain of monoclonal antibody no. 81, and/or the light chain thereof.

Yet another such ligand includes the amino acid sequence for antibody against the "stalk" region, i.e. from the about amino acid thr-181 to about amino acid 235-asp.

The ligands may comprise e.g. proteins, peptides, immunoadhesins, antibodies or other organic compounds.

The proteins may comprise, for example, a fusion protein of the ligand with another protein, optionally linked by a peptide linker. Such a fusion protein can increase the retention time of the ligand in the body, and thus may even allow the ligand-protein complex to be employed as a latent agent or as a vaccine.

The term "proteins" includes muteins and fused proteins, their salts, functional derivatives and active fractions "Functional derivatives" as used herein cover derivatives of the ligands and their fused proteins and muteins, which may be prepared from the functional groups which occur as side chains on the residues or the N- or C- terminal groups, by means known in the art, and are included in the invention as long as they remain pharmaceutically acceptable, i.e. they do not destroy the activity of the ligand and do not confer toxic properties on compositions containing it. These derivatives may, for example, include polyethylene glycol side-chains which may mask antigenic sites and extend the residence of the ligands in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of the ligands, its fused proteins and its muteins, the present invention covers any fragment or precursors of the polypeptide chain of the ligand alone or together with associated molecules or residues linked thereto, e.g. sugar or phosphate residues, or aggregates of the protein molecule or the sugar residues by themselves, provided said fraction has the same biological and/or pharmaceutical activity.

As used herein the term "muteins" refers to analogs of the proteins, peptides and the like in which one or more of the amino acid residues of the protein found to bind are replaced by different amino acid residues or are deleted, or one or more amino acid residues are added to the original sequence, without changing considerably the activity of the resulting product. These muteins are prepared by known synthesis and/or by site-directed mutagenesis techniques, or any other known technique suitable therefor.

The term "fused protein" refers to a polypeptide comprising the ligands or a mutein thereof fused with another protein which has an extended residence time in body fluids. The ligands may thus be fused to another protein, polypeptide or the like, e.g. an immunoglobulin or a fragment thereof.

The term "salts" herein refers to both salts of carboxyl groups and to acid addition salts of amino groups of the ligands, muteins and fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

The peptides include peptide bond replacements and/or peptide mimetics, i.e. pseudopeptides, as known in the art (see e.g. Proceedings of the 20th European Peptide Symposium, ed. G. Jung, E. Bayer, pp. 289–336, and references therein), as well as salts and pharmaceutical preparations and/or formulations which render the bioactive peptide(s) particularly suitable for oral, topical, nasal spray, ocular, pulmonary, I.V. or subcutaneous delivery, depending on the particular treatment indicated. Such salts, formulations, amino acid replacements and pseudopeptide structures may be necessary and desirable to enhance the stability, formulation, deliverability (e.g. slow release, prodrugs), or to improve the economy of production, as long as they do not adversely affect the biological activity of the peptide.

Besides substitutions, three particular forms of peptide mimetic and/or analogue structures of particular relevance when designating bioactive peptides, which have to bind to a receptor while risking the degradation by proteinases and peptidases in the blood, tissues and elsewhere, may be mentioned specifically, illustrated by the following examples: Firstly, the inversion of backbone chiral centres leading to D-amino acid residue structures may, particularly at the N-terminus, lead to enhanced stability for proteolytical degradation without adversely affecting activity. An example is given in the paper "Tritriated D-ala$^1$-Peptide T Binding", Smith C. S. et al., Drug Development Res. 15, pp. 371–379 (1988). Secondly, cyclic structure for stability, such as N to C interchain imides and lactames (Ede et al. in Smith and Rivier (Eds.) "Peptides: Chemistry and Biology", Escom, Leiden (1991), pp. 268–270), and sometimes also receptor binding may be enhanced by forming cyclic analogues. An example of this is given in "Confirmationally restricted thymopentin-like compounds", U.S. Pat. No. 4,457,489 (1985), Goldstein, G. et al. Thirdly, the introduction of ketomethylene, methylsuflide or retroinverse bonds to replace peptide bonds, i.e. the interchange of the CO and NH moieties are likely to enhance both stability and potency. An example of this type is given in the paper "Biologically active retroinverso analogues of thymopentin", Sisto A. et al in Rivier, J. E. and Marshall, G. R. (eds) "Peptides, Chemistry, Structure and Biology", Escom, Leiden (1990), pp. 722–773).

The peptides of the invention can be synthesized by various methods which are known in principle, namely by chemical coupling methods (cf. Wunsch, E: "Methoden der organischen Chemie", Volume 15, Band 1+2, Synthese von Peptiden, thime Verlag, Stuttgart (1974), and Barrany, G.; Marrifield, R. B.: "The Peptides", eds. E. Gross, J. Meienhofer, Volume 2, Chapter 1, pp. 1–284, Academic Press (1980)), or by enzymatic coupling methods (cf. Widmer, F. Johansen, J. T., Carlsberg Res. Commun, Vol. 44, pp. 37–46 (1979), and Kullman, W.: "Enzymatic Peptide Synthesis" CRC Press Inc. Boca Raton, Fla. (1987), and Widmer, F., Johansen, J. T. in "Synthetic Peptides in Biology and Medicines:, eds. Alitalo, K., Partanen, P., Vatieri, A., pp. 79–86, Elsevier, Amsterdam (1985)), or by a combination of chemical and enzymatic methods if this is advantageous for the process design and economy.

A cysteine residue may be added at both the amino and carboxy terminals of the peptide, which will allow the cyclisation of the peptide by the formation of a di-sulphide bond.

Any modifications to the peptides of the present invention which do not result in a decrease in biological activity are within the scope of the present invention.

There are numerous examples which illustrate the ability of anti-idiotypic antibodies (anti-Id Abs) to an antigen to function like that antigen in its interaction with animal cells and components of cells. Thus, anti-Id Abs to a peptide hormone antigen can have hormone-like activity and interact specifically with a mediator in the same way as the receptor does. (For a review of these properties see: Gaulton, G. N. and Greane, M. I. 1986. Idiotypic mimicry of biological receptors, Ann. Rev. Immunol. Vol. 4, pp. 253–280; Sege K. and Peterson, P. A., 1978, Use of anti-idiotypic antibodies as cell surface receptor probes, Proc. Natl. Acad. Sci. U.S.A., Vol. 75, pp. 2443–2447).

It is expected from this functional similarity of anti-Id Ab and antigen, that anti-Id Abs bearing the internal image of an antigen can induce immunity to such an antigen. (See review in Hiernaux, J. R., 1988, Idiotypic vaccines and infectious diseases, Infect. Immun., Vol. 56, pp. 1407–1413).

It is therefore possible to produce anti-idiotypic antibodies to the peptides of the present invention which will have similar biological activity.

Accordingly, the present invention also provides anti-idiotypic antibodies to the peptides of the present invention, the anti-idiotypic antibody being capable of inhibiting TNF toxicity, but not its binding to the receptor.

The individual specificity of antibodies resides in the structures of the peptide loops making up the Complementary Determining Regions (CDRs) of the variable domains of the antibodies. Since in general the amino acid sequence of the CDR peptides of an anti-Id Ab are not identical to or even similar to the amino acid sequence of the peptide antigen from which it was originally derived, it follows that peptides whose amino acid sequence in quite dissimilar, in certain contexts, can take up a very similar three-dimensional structure. The concept of this type of peptide, termed a "functionally equivalent sequence" or mimotope by Geyson is known. (Geyson, H. M. et al, 1987, Strategies for epitope analysis using peptide synthesis., J. Immun. Methods, Vol. 102, pp. 259–274).

Moreover, the three-dimensional structure and function of the biologically active peptides can be simulated by other compounds, some not even peptidic in nature, but which nevertheless mimic the activity of such peptides. This field is summarized in a review by Goodman, M. (1990). (Synthesis, Spectroscopy and computer simulations in peptide research, Proc. 11th American Peptide Symposium published in *Peptides-Chemistry, Structure and Biology*, pp. 3–29; Eds. Rivier, J. E. and Marshall, G. R. Publisher Escom).

It is also possible to produce peptide and non-peptide compounds having the same three-dimensional structure as the peptides of the present invention. These "functionally equivalent structures" or "peptide mimics" will react with antibodies raised against the peptide of the present invention and may also be capable of inhibiting TNF toxicity.

Accordingly, a further embodiment of the present invention provides a compound the three-dimensional structure of which is similar as a pharmacophore to the three-dimensional structure of the peptides of the present invention, the compound being characterized in that it reacts with antibodies raised against the peptides of the present invention and that the compound is capable of inhibiting TNF toxicity.

More detail regarding pharmacophores can be found in Bolin et al., p. 150, Polinsky et al., p. 287, and Smith et al., p. 485, in Smith and Rivier (eds.) "Peptides: Chemistry and Biology", Escom, Leiden (1991).

All of the molecules (proteins, peptides, etc.) may be produced either by conventional chemical methods, as described herein, or by recombinant DNA methods.

The invention also provides DNA molecules encoding the ligands according to the invention, vectors containing them and host cells comprising the vectors and capable of expressing the ligands according to the invention.

The host cell may be either prokaryotic or eukaryotic.

The invention further provides DNA molecules hybridizing to the above DNA molecules and encoding ligands having the same activity.

The invention also provides pharmaceutical compositions comprising the above ligands which are useful for treating diseases induced or caused by the effects of TNF, either endogenously produced or exogenously administered.

The invention also provides for using the ligands according to the invention for increasing the inhibitory effect of a soluble receptor of the TNF/NGF receptor family. As stated above, the soluble receptors, especially those of TNF, have the ability to block the function of TNF by binding it in competition with the surface receptors. Application of a ligand according to the invention together with a soluble receptor is therefore expected to increase the inhibitory effect of the soluble receptor.

BRIEF DESCRIPTION OF THE FIGURES

FIG. 2 shows the nucleotide (SEQ ID NO:1) and deduced amino acid (SEQ ID NO:2) sequences of the p75 receptor. TBP-II and transmembranal domains are boxed and shaded. The region recognized by the group 67 antibodies is underlined, and the region recognized by the anti-stalk antibodies is underlined by a broken line.

FIG. 7 shows that antibodies against the upper part of the extracellular domain of the p75 TNF-R do not signal in A9 cells which express the cytoplasmically truncated p75 TNF-R. Antibodies of the 67 group do have, though, an inhibitory effect on TNF function in them (not shown).

FIG. 8 shows that antibodies against the 67 epitope impede TNF dissociation from p75 TNF-R.

FIG. 9 shows the sequence homology between several members of the TNF/NGF receptor family.

DETAILED DESCRIPTION OF THE INVENTION

Figure 1:
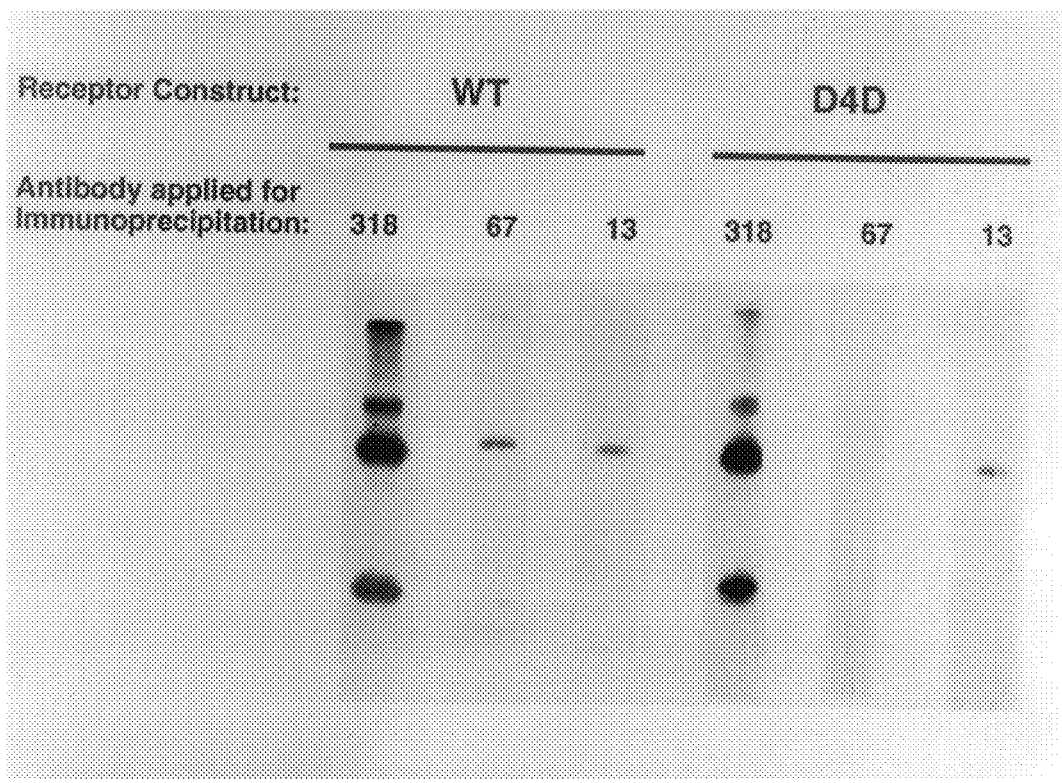
FIG. 1 shows the results of the test by which epitope 67 was mapped.

TNF, as stated above, is a cytokine which initiates its effect on cell function by binding to two specific cell surface receptors: the p55 and p75 receptors. Binding of antibodies to the extracellular domain of these receptors can interfere with its effect. However, as shown in a number of studies, antibodies binding to the extracellular domain of the receptors can also trigger the effects of TNF by inducing aggregation of the p55 receptors, as well as by inducing aggregation of the p75 receptors. (Engelmann, et al. J. Biol. Chem., Vo. 265, No. 24, pp. 14497–14504, 1990; and unpublished data).

As disclosed in patent application Ser. No. 103051, antibodies binding to one particular region in the p75 receptor are not mimetic but rather inhibitory to the signalling for the cytocidal effect by this receptor. This, in spite of the fact that when binding to this region, these antibodies do not block TNF binding, but rather increase it to some extent. In application Ser. No. 106,271 this region is more particularly identified as extending between cys-163 and thr-179, in the fourth cysteine rich domain of the receptor. The present invention reveals that the region recognized by certain other antibodies is the region extending downstream of thr-181 and upstream of cys-163 to about cys-142 in the extracellular domain of the p75 receptor.

The present invention also reveals that the so-called "stalk-antibody" recognizes a region downstream of the fourth cysteine rich domain, more particularly the region extending from about amino acid 181 to about amino acid 235.

It was also found in accordance with the present invention that, in case of the "67 epitope" antibodies, the divalent antibodies have an effect which mimics TNF action, while the monovalent fragments, such as F(ab), inhibit the cytotoxic effect of TNF.

Based on these findings, small molecular weight compounds, such as peptides or mimetic compounds, which will either inhibit the function of the p75 receptor, or enhance it, can be defined.

In view of these findings, as well as the close similarity of the receptors in this particular family, this invention relates also to ligands which bind to the same regions in the extracellular domain of the various other members of the TNF/NGF receptor family and modulate the function of the other receptors, similarly to the modulation of the function of TNF. In this receptor family, the localization of cysteines in the extracellular domain and the spacing is highly conserved. Certain members of this family, e.g. CDw40, exhibit particularly high similarity to the p75 receptor. Particularly in such receptors, ligands binding to these regions are expected to have effects similar to the effect of the ligands according to the present invention on the p75 receptor.

Recombinant production of the ligands is carried out by known methods commonly employed in the art.

The invention is illustrated by the following non-limiting examples:

EXAMPLE 1

Monoclonal Antibodies to TBP-II

Production of the monoclonal antibodies

Female Balb/C mice (8 weeks old) were injected with 1 $\mu$g purified TBP-II in an emulsion of complete Freund's adjuvant into the hind foot pads, and three weeks later, subcutaneously into the back in incomplete Freund's adjuvant. The other injections were given in weekly intervals, subcutaneously in PBS. Final boosts were given 4 days (i.p.) and 3 days (i.v.) before the fusion with 9.0 $\mu$g of TBP-I in PBS. Fusion was performed using NSO/Mr cells and lymphocytes prepared from both the spleen and the local lymphocytes of the hind legs as fusion partners. The hybridomas were selected in DMEM supplemented with HAT, 15% horse serum and gentamycin 2 $\mu$g/ml. Hybridomas that were found to produce antibodies to TBP-I were subcloned by the limiting dilution method and injected into Balb/C mice that had been primed with pristane for the production of ascites. Immunoglobulins were isolated from the ascites by ammonium sulfate precipitation (50% saturation) and then dialyzed against PBS containing 0.02% azide. Purity was approximately 60% as estimated by analysis on SDS-PAGE and staining with Commassie blue. The isotypes of the antibodies were defined with the use of a commercially available ELISA kit (Amersham, U.K.).

Several positive clones were obtained, subcloned for further studies and characterized. Some of the isolated subclones with their isotype and binding of TBP-II in inverted RIA are listed in Table I.

TABLE I

Subclones producing monoclonal antibodies to TBP-II

| Clone number | Screening with iRIA [CPM] | Screening of subclone with iRIA [CPM] | Isotype |
| --- | --- | --- | --- |
| 13.11 | 31800 | 31000 | $IgG_1$ |
| .12 |  | 31500 | $IgG_1$ |
| .13 |  | 31100 | $IgG_1$ |
| 14.1 | 15300 | 15400 | $IgG_{2a}$ |
| .6 |  | 16200 | $IgG_{2a}$ |
| .7 |  | 15300 | $IgG_{2a}$ |
| 20.2 | 12800 | 14200 | $IgG_{2b}$ |
| .5 |  | 14300 | $IgG_{2b}$ |
| .6 |  | 14800 | $IgG_{2b}$ |
| 22.7 | 20400 | 20000 | $IgG_1$ |
| .8 |  | 19300 | $IgG_1$ |
| 27.1 | 18000 | 27000 | $IgG_{2a}$ |
| .3 |  | 25000 | $IgG_{2a}$ |
| .9 |  | 28000 | $IgG_{2a}$ |
| 32.4 | 11315 | 10900 | $IgG_{2b}$ |
| .5 |  | 10700 | $IgG_{2b}$ |
| .6 |  | 11200 | $IgG_{2b}$ |
| 33.1 | 18400 | 11400 | $IgG_1$ |
| .3 |  | 10500 | $IgG_1$ |
| .4 |  | 14800 | $IgG_1$ |
| 36.1 | 27500 | 26600 | $IgG_{2a}$ |
| .5 |  | 24900 | $IgG_{2a}$ |
| .6 |  | 24900 | $IgG_{2a}$ |
| 41.3 | 13800 | 18100 | $IgG_1$ |
| .7 |  | 18100 | $IgG_1$ |
| .10 |  | 18800 | $IgG_1$ |
| 67.1 | 16800 | 10900 | $IgG_{2a}$ |
| .16 |  | 10800 | $IgG_{2a}$ |
| .17 |  | 10900 | $IgG_{2a}$ |
| 70.2 | 15100 | 5100 | $IgG_{2a}$ |
| .3 |  | 5200 | $IgG_{2a}$ |
| .4 |  | 5300 | $IgG_{2a}$ |
| 77.2 | 15300 | 11800 | $IgG_{2b}$ |
| 78.9 | 25300 | 21400 | $IgG_{2a}$ |
| 82.1 | 17600 | 25900 | $IgG_1$ |
| .4 |  | 25700 | $IgG_1$ |
| .10 |  | 26400 | $IgG_1$ |
| 86.2 | 8800 | 12200 | $IgG_{2b}$ |
| .5 |  | 12600 | $IgG_{2b}$ |
| .11 |  | 12800 | $IgG_{2b}$ |
| 19.6 |  | 29700 | $IgG_{2a}$ |
| .9 |  | 28900 | $IgG_{2a}$ |

Hybridomas TBP-II 13-12 and TBP-II 70-2 were deposited with the Collection Nationale de Cultures de Microorganismes (CNCM), Institut Pasteur, 25, rue du Docteur Roux, 75724 Paris CEDEX 15, France on Mar. 12, 1990 and were assigned No. I-929 and No. I-928, respectively.

EXAMPLE 2

Inverted Radioimmunoassay (iRIA) for the Detection of the Monoclonal Antibodies to TBP-II This assay was used for estimating the level of the anti-TBP antibodies in the sera of the immunized mice and for screening for the production of the antibodies by hybridomas. PVC, 96-well microtiter plates (Dynatech 1-220-25) were coated for 12 hr at 4° C. with affinity purified goat anti mouse F(ab) immunoglobulins (Biomakor, Israel 10 $\mu$g/ml in PBS containing 0.02% $NaH_3$), then blocked for 2 hr at 37° C. with 0.5% BSA in PBS supplemented with 0.05% Tween 20 (Sigma) and 0.02% $NaH_3$ (blocking buffer) and washed 3 times with PBS containing 0.5% Tween 20 and 0.02% $NaH_3$ (washing buffer). Serum samples, in serial dilutions, or samples of hybridoma growth media (50 $\mu$l) were applied into the walls for 2 hr at 37° C. The plates were rinsed with washing buffer and $^{125}$I-labelled TBP-I (10,000 cpm, in blocking buffer) was applied into the walls. After further incubation of 2 hr at 37° C., the plates were washed and the amount of label which bound to individual wells was determined in the gamma-counter.

EXAMPLE 3

The Use of Anti-TBP-II Antibodies for Affinity Chromatography

Antibodies against TBP-II can be utilized for the purification of TBP-II by affinity chromatography, according to the following procedure. The monoclonal antibodies for affinity chromatography were selected by testing their binding capacity for the radiolabeled antigen in a solid phase radio immunoassay. Ascites from all hybridomas was purified by ammonium sulfate precipitation at 50% saturation followed by extensive dialysis against PBS. PVC 96-well plates were coated with the purified McAbs, and after blocking the plates with PBS containing 0.5% BSA, 0.05% Tween 20 (Sigma) and 0.02% NaH$_3$, the wells were incubated with 50,000 cpm $^{125}$I-TNF for 2 h at 37° C., then washed and the radioactivity which had bound to each well was quantitated in the gamma-counter. The antibodies with the highest binding capacity were examined for their performance in immunoaffinity chromatography.

Polyacryl hydrazide agarose was used as resin to immobilize the antibodies. The semipurified immunoglobulins were concentrated and coupled to the resin as specified by Wilchek and Miron, *Methods in Enzymology* 34:72–76, 1979. Three monoclonal antibodies against TBP-I, clones 16, 20, and 34 were tested in these experiments. Antibody columns of 1 ml bed were constructed. Before use, all columns were subjected to 10 washed with the elution buffer, each wash followed by neutralization with PBS. Then the columns were loaded with 120 ml of concentrated urinary proteins in PBS with 0.02% NaH$_3$. The flow rate of the columns was adjusted to 0.2 to 0.3 ml per minute. After loading, the columns were washed with 50 ml PBS and then eluted with a solution containing 50 mM citric acid, pH 2.5, 100 mM NaCl and 0.02% NaH$_3$. Fractions of 1 ml were collected. Samples of the applied urinary proteins, the last portion of the wash (1 ml) and of each elution fraction (8 fractions of 1 ml per column) were taken and tested for protein concentration and activity in the bioassay for TBP-II. According to the protein measurements before and after coupling of the antibodies to hydrazide agarose, the amounts of immunoglobulin bound to the columns ranged from 7 to 10 mg/ml agarose. All protein measurements were done according to a micro-flurescamin method in comparison to a standard solution containing 100 μg BSA/ml (Stein, S. and Moschera, J., *Methods Enzymol.* 79:7–16, 1981).

EXAMPLE 4

Determination of TBP-II using Anti-TBP-II Antibodies

The levels of TBP-II in the sera of healthy individuals, patients with cancer or systemic lupus erthematosus (SLE) and of pregnant women at term were determined by an ELISA method employing a monoclonal antibody to TBP-II coating the plates. 50 μl of each sample was added and after a 2.5 h incubation at 37° C. the wells were washed with a solution of PBS, Tween 0.05% and sodium azide 0.02%, after which a rabbit anti-TBP-II polyclonal antibody was added for 2.5 h at 37° C. Then the wells were washed again (no azide) and goat anti-rabbit horseradish peroxidase-coupled antibody was added for 2 h. Following this incubation, and washing, an ABTS buffer was added and optical density (O.D.) read 30 min. later at 600 nm.

The normal levels of TBP-II in human serum of healthy individuals as determined by the ELISA method are 1.48±0.46 ng/ml.

EXAMPLE 5

Epitope Mapping of TBP-II by Cross Competition Analysis with Monoclonal Antibodies (mAbs) to TBP-II PVC 96-well microtiter plates were coated as described above, with purified mAbs to TBP-II (25 μg/ml). Following rinsing and blocking, samples of $^{125}$I-labelled TBP-II (100, 000 cpm per well) which had been preincubated for 2 h, at 37° C. with the same or a different monoclonal antibody to TBP-II (at 1 μg/ml) were put into the wells; the plates were incubated overnight at 4° C., washed and the radioactivity bound to each well was determined by gamma-counting. The results are expressed as percent of the control values (TBP-II binding in the absence of competing mAbs).

The results are depicted in Table II. The monoclonal antibodies are indicated by the clone numbers in the first row and in left column. Low percent binding values indicate that the two antibodies compete for each other's epitope on TBP-II, while higher values indicate that they bind to different epitopes. Non-competitive antibodies are suitable for use in double-sandwich ELISA, e.g., clones 13 and 70.

TABLE II

Cross competition analysis with monoclonal antibodies to TBP II

| | solid phase antibodies | | | | | | | | | | | | | | | |
|---|---|---|---|---|---|---|---|---|---|---|---|---|---|---|---|---|
| | 13 | 14 | 19 | 20 | 22 | 27 | 32 | 33 | 36 | 41 | 67 | 70 | 77 | 78 | 82 | 86 |
| competitor antibody | | | | | | | | | | | | | | | | |
| 13 | 4 | 64 | 53 | 73 | 31 | 51 | 161 | 35 | 177 | 72 | 131 | 128 | 77 | 102 | 50 | 101 |
| 14 | 119 | 20 | 90 | 13 | 13 | 84 | 156 | 11 | 132 | 173 | 134 | 113 | 14 | 70 | 89 | 179 |
| 19 | 103 | 28 | 7 | 19 | 11 | 5 | 144 | 11 | 144 | 133 | 179 | 123 | 18 | 5 | 85 | 126 |
| 20 | 119 | 17 | 93 | 14 | 10 | 88 | 149 | 9 | 135 | 170 | 137 | 135 | 16 | 70 | 101 | 181 |
| 22 | 109 | 26 | 94 | 22 | 13 | 82 | 128 | 12 | 115 | 164 | 136 | 114 | 17 | 68 | 98 | 167 |
| 27 | 106 | 23 | 11 | 27 | 14 | 8 | 145 | 17 | 152 | 133 | 196 | 136 | 24 | 8 | 82 | 125 |
| 32 | 150 | 267 | 150 | 291 | 156 | 186 | 14 | 163 | 139 | 200 | 205 | 18 | 294 | 143 | 103 | 226 |
| 33 | 115 | 19 | 98 | 23 | 16 | 86 | 133 | 12 | 118 | 156 | 120 | 114 | 24 | 78 | 90 | 155 |
| 36 | 155 | 262 | 168 | 271 | 144 | 185 | 167 | 158 | 12 | 169 | 223 | 135 | 265 | 158 | 93 | 150 |
| 41 | 117 | 119 | 119 | 118 | 101 | 109 | 118 | 76 | 93 | 9 | 179 | 107 | 106 | 111 | 8 | 9 |
| 67 | 112 | 138 | 125 | 141 | 125 | 157 | 136 | 107 | 138 | 213 | 30 | 117 | 120 | 127 | 106 | 236 |
| 70 | 150 | 246 | 150 | 255 | 145 | 166 | 4 | 162 | 166 | 217 | 204 | 6 | 232 | 132 | 107 | 234 |
| 77 | 121 | 18 | 98 | 15 | 13 | 78 | 148 | 11 | 145 | 184 | 142 | 132 | 18 | 66 | 103 | 184 |
| 78 | 118 | 20 | 9 | 26 | 10 | 6 | 153 | 13 | 157 | 137 | 183 | 131 | 19 | 6 | 94 | 172 |
| 82 | 107 | 110 | 130 | 116 | 112 | 121 | 128 | 89 | 90 | 8 | 162 | 102 | 121 | 113 | 8 | 7 |

TABLE II-continued

Cross competition analysis with monoclonal antibodies to TBP II

| | solid phase antibodies | | | | | | | | | | | | | | | |
|---|---|---|---|---|---|---|---|---|---|---|---|---|---|---|---|---|
| | 13 | 14 | 19 | 20 | 22 | 27 | 32 | 33 | 36 | 41 | 67 | 70 | 77 | 78 | 82 | 86 |
| 86 | 122 | 181 | 125 | 166 | 126 | 129 | 131 | 120 | 86 | 18 | 253 | 109 | 152 | 125 | 20 | 17 |
| 100% value | 31582 | 3958 | 2057 | 5437 | 4947 | 17395 | 25923 | 3525 | 6368 | 8042 | 4368 | 24113 | 5887 | 22222 | 11608 | 9703 |

EXAMPLE 6

Mapping of the Epitope 67 of the p75 TNF-R a) In order to compare the function of the 67 group antibodies, not only to antibodies which bind to the receptor at the 67 epitope region, but also to antibodies that bind to the receptor downstream to that epitope region, we immunized rabbits with a chimeric construct corresponding to the region extending downstream to the 32 epitope (amino acids 181 to 235; the "stalk" region), linked to MBP. The rabbits developed antibodies which bound to the chimera with which they were immunized as well as to the intact p55 TNF receptor. These antibodies were affinity purified by binding to the chimeric protein, linked to an Affigel 10 column, and tested for effect on TNF function and binding. (The affinity purified antibody preparation was termed "318").

b) The mapping of epitope 67 was carried out by examining the ability of antibodies number 67 and 13 (an antibody that binds to the upper part of the extracellular domain of the p75 TNF-R) as well as antiserum 318, to immunoprecipitate the following methionine-labeled soluble p75 TNF-R mutants: WT—a receptor extending from amino acid 22 to amino acid 234, D4D—a receptor like WT, from which the 4th cysteine-rich domain has been deleted (amino acids 141 to 180). The receptors were produced by in vitro transcription of cDNAs encoding them (from the Bluescript vector, using the T7 promoter) followed by in vitro translation using the Promega TnT kit. The immunoprecipitated proteins were analyzed by SDS PAGE, followed by autoradiography. (A) Immunoprecipitation of WT. All antibodies were effective. (B) Immunoprecipitation of D4D. Only antibodies 13 and 318 were effective. The findings indicate that epitope 67 is located at the upper part of the 4th cysteine rich domain, within about amino acids 141 to 180.

EXAMPLE 7

Figure 3:
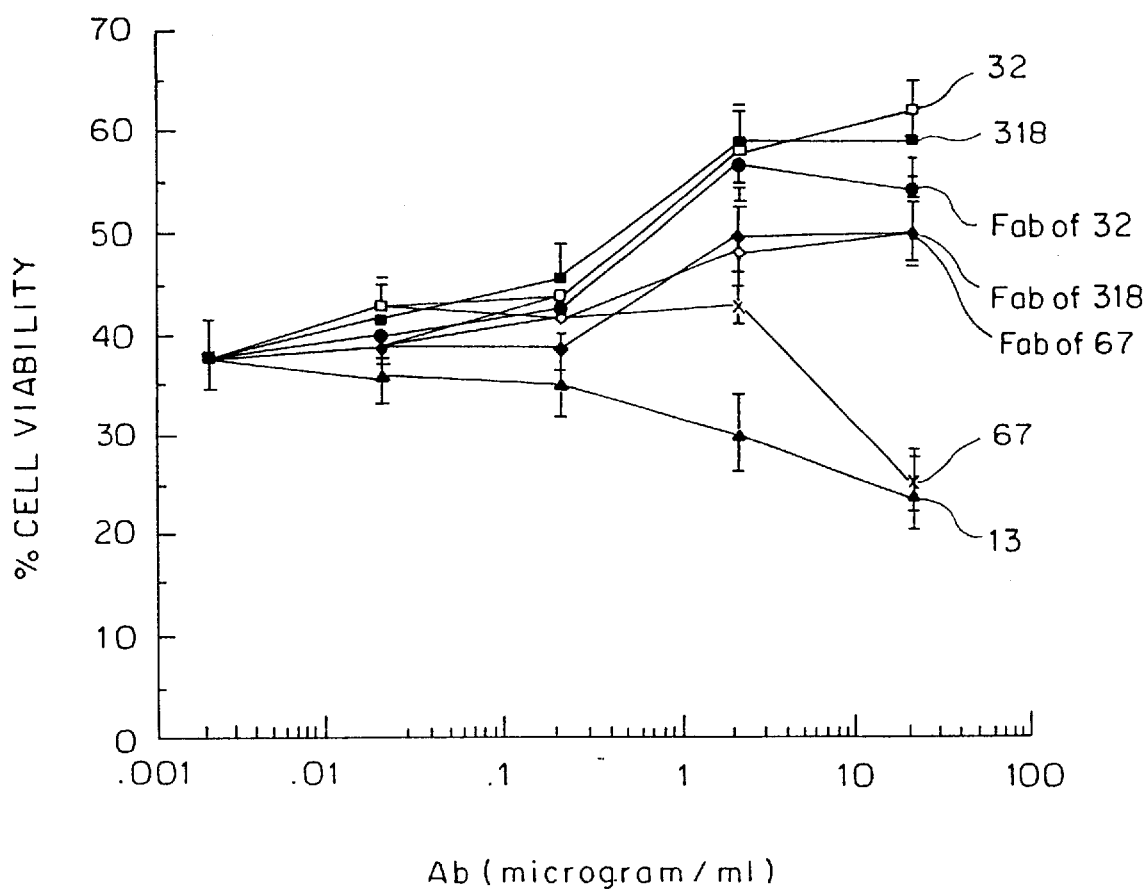
FIG. 3 shows the inhitory effect of the 67 and anti-stalk antibodies on TNF function in HeLa cells.

Titration of the Inhibitory Effect of the Group 67 Antibodies and the Anti-stalk Antibodies on TNF Function As shown in FIG. 3, the protective effect of the different antibodies studied on the cytocidal effect of TNF on HeLa p75.3 cells was found to vary depending on the particular antibody used: antibodies 32 and antiserum 318 and their Fab monovalent fragments, which protect, antibody 67, which protects as Fab monovalent fragment and enhances TNF cytotoxicity in its divalent form, and antibody 13 (which binds to the upper part of the extracellular domain of the -75-R) which enhances the cytocidal effect of TNF (p75.3 cells are HeLa cells transfected with the full length p75 TNF-R).

EXAMPLE 8

Figure 4:
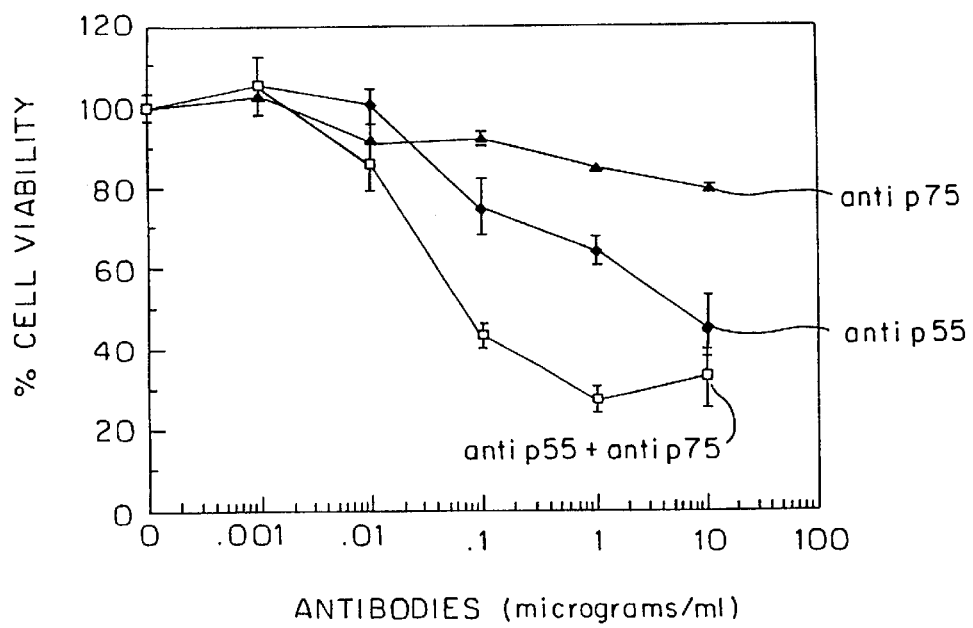
FIG. 4 shows that antibodies against the upper part of extracellular domain of the p75 TNF-R are signalling in the HeLa cells.
Figure 5:
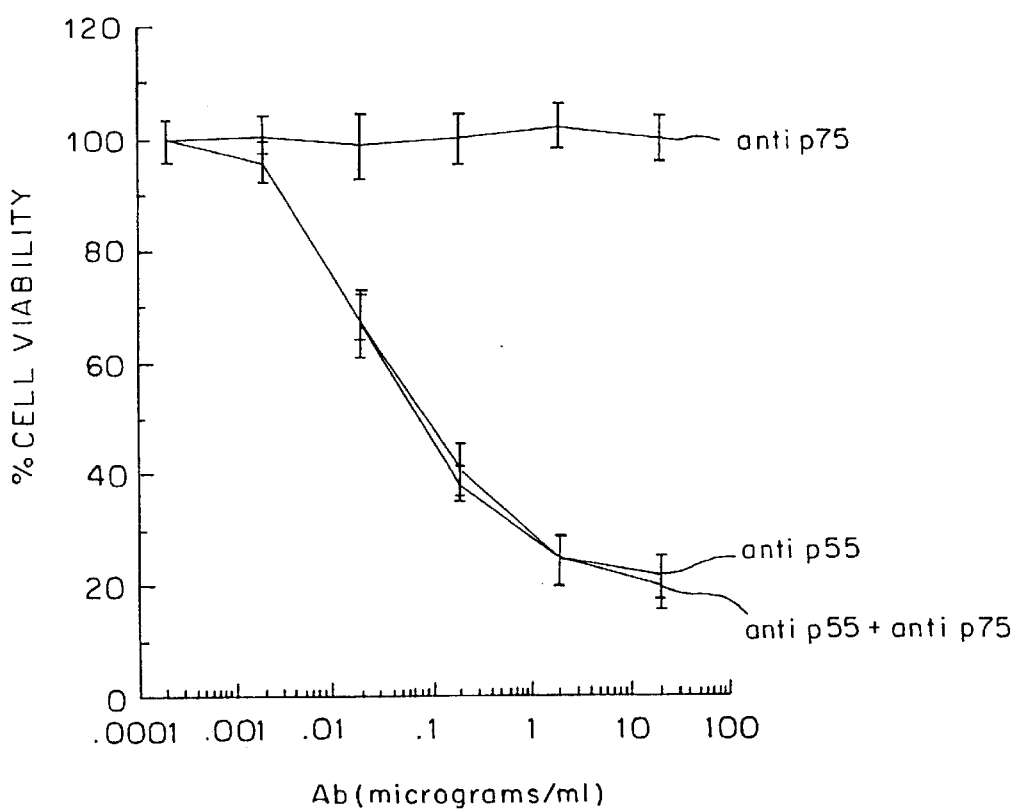
FIG. 5 shows that antibodies against the upper part of the extracellular domain of the p75 TNF-R do not signal in A9 cells which express the human p75 TNF-R. Antibodies of the 67 group do have, though, an inhibitory effect on TNF funtion in them (FIG. 6).
Figure 6:
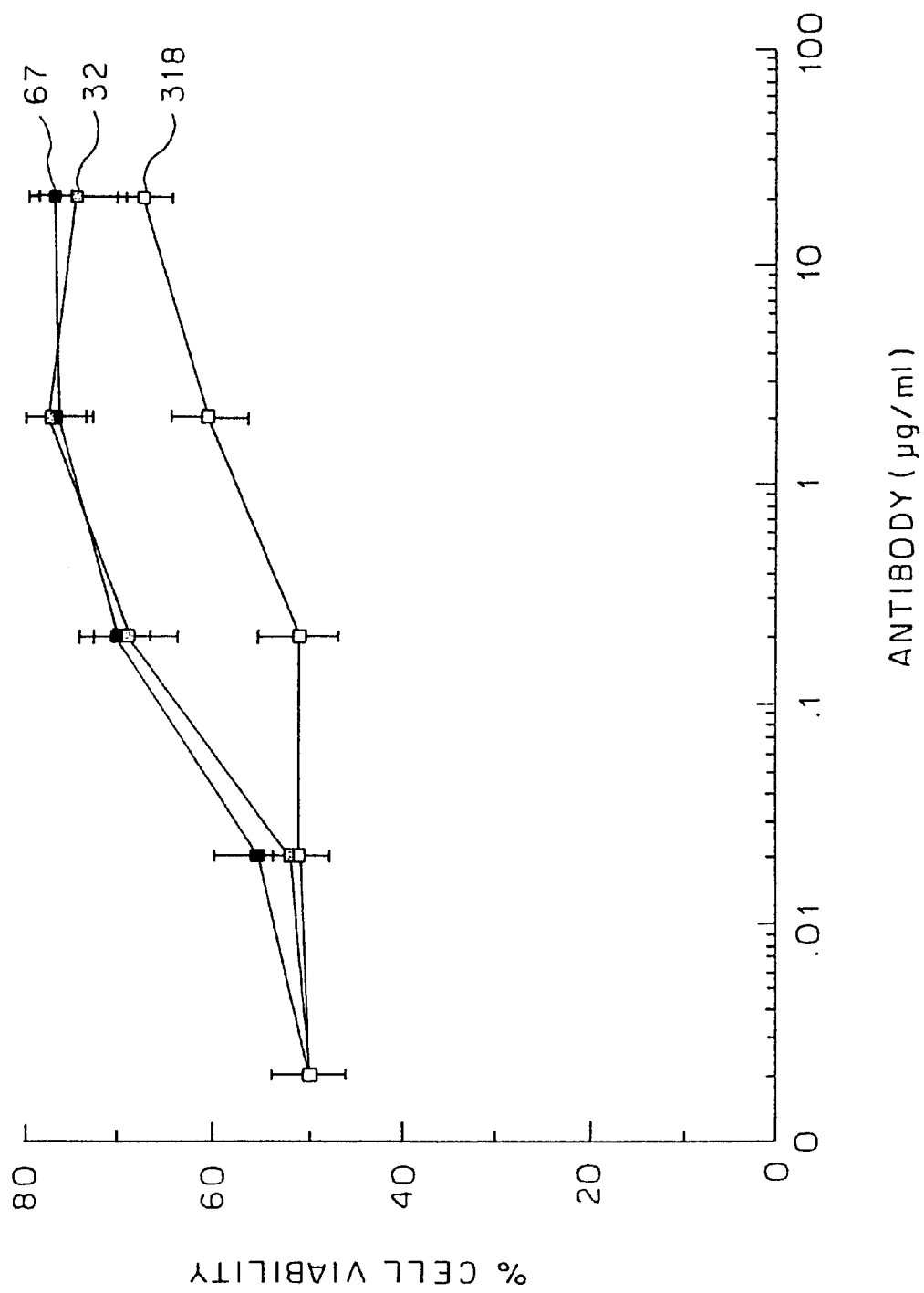
FIG. 6 shows that antibodies against the upper part of the extracellular domain of the p75 TNF-R inhibit TNF function in A9 cells.

The Inhibitory Effect of the Group 67 and Anti-stalk Antibodies is Independent of the Expression and Function of the Intracellular Domain of the p75 TNF-R In HeLa cells which over-express the p75 TNF-R, antibodies against the upper part of the extracellular domain of the receptor have a cytocidal effect, synergistic with that of antibodies against the p55-R (FIG. 4). However, these antibodies do not have such an effect in A9 cells which express either the full-length or cytoplasmically-truncated human p75 TNF-R (FIGS. 5 and 7, respectively). However, antibodies which bind to the lower part of the receptor did show inhibitory effect on TNF function even in these cells, irrespective of whether the cells expressed the full-length or the cytoplasmically truncated receptor (see FIG. 6 as well as data not shown).

EXAMPLE 9

Effect of the Various Antibodies on the Dissociation of TNF Form p75 TNF-R

FIG. 8 shows a comparison of the rate of the dissociation of TNF from the p55 TNF-R, as assessed by measuring the dissociation of radiolabeled TNF from mouse A9 cells expressing transfected human p55 TNF-R (A9D2 cells, in which over 90% of the cell-bound TNF is associated with the human p55 TNF-R) and from the HeLa p75.3 cells, in which most of the bound TNF is associated with the overexpressed p75 TNF-R. As opposed to the very slow dissociation of TNF from the p55 TNF-R, TNF dissociates rather rapidly from the p75 TNF-R.

FIG. 8 also illustrates the effect of antibodies that bind to various regions at the bottom of the extracellular domain of the p75 TNF-R on the dissociation of TNF from the receptor: Antibody 32 (that binds to the "32 epitope") as well as its Fab monovalent fragments, antibody 67—that binds to the 67 epitope, as well as antiserum 318, raised against the "stalk" region at the bottom of the extracellular domain, are all shown to impede the dissociation of TNF from the receptor.

EXAMPLE 10

FIG. 9 shows the internal cystein rich repeats in the extracellular domains of the two TNF-Rs and their alignment with the homologous repeats in the extracellular domain of the human FAS, nerve growth factor receptor (NGF) and CDw40, as well as rat Ox40. The amino acid sequences (one letter symbols) are aligned for maximal homology. The positions of the amino acids within the receptors are denoted in the left hand margin.

Deposit Information

Hybridomas TBP-II 67 and 81 were deposited with the Collection National De Cultures de Microorganismes (CNCM), Institut Pasteur 25, rue du Docteur Roux, 75724 Paris Cedex 15, France, on Oct. 11, 1993 and assigned No.s I-1368 and I-1369, respectively.

What is claimed is:

1. A peptide or antibody, which peptide or antibody inhibits the cytocidal effect of TNF but does not block TNF binding to the p75 TNF receptor, said peptide or antibody comprising the antigen binding portion of an antibody which binds to the fourth cysteine rich domain of the p75 TNF receptor, which domain consists of the sequence of amino acid residues 163 to 201 of SEQ ID NO:2, or to the region between said fourth cysteine rich domain of the p75 TNF receptor and the cell membrane, which region consists of the sequence of amino acid residues 202–257 of SEQ ID NO:2, with the proviso that said antigen binding portion is not that of a monoclonal antibody from the clone 67 (CNCM No. I-1368).

2. A peptide or antibody in accordance with claim 1 which comprises the antigen binding portion of an antibody which binds to the amino acid sequence of residues 163 to 185 of SEQ ID NO:2, with the proviso that said antigen binding portion is not that of a monoclonal antibody from the clone 67 (CNCM No. I-1368).

3. A peptide or antibody in accordance with claim 1 which comprises the antigen binding portion of an antibody which binds to the p75 TNF receptor in a region which comprises thr-179 to the end of the extracellular domain thereof, which region consists of the sequence of amino acid residues 201–257 of SEQ ID NO:2.

4. An antibody or a peptide which binds to TBP-II (residues 27–210 of SEQ ID NO:2), comprising a fraction of monoclonal antibody 67 (CNCM No. I-1368), which fraction binds to TBP-II.

5. An antibody or peptide comprising monoclonal antibody 67 (CNCM No. I-1368).

* * * * *

UNITED STATES PATENT AND TRADEMARK OFFICE
CERTIFICATE OF CORRECTION

| | | |
|---|---|---|
| PATENT NO. | : 6,262,239 B1 | Page 1 of 1 |
| APPLICATION NO. | : 08/476862 | |
| DATED | : July 17, 2001 | |
| INVENTOR(S) | : Wallach et al. | |

It is certified that error appears in the above-identified patent and that said Letters Patent is hereby corrected as shown below:

Title Page, insert the following:

-- Related U.S. Application Data

(60)    Continuation-in-part of application No. 07/930,443, filed on August 19, 1992, and a continuation-in-part of application No. 08/321,685, filed on October 12, 1994, now abandoned. Application No. 07/930,443, filed on August 19, 1992, is a continuation of application No. 07/524,263, filed May 16, 1990, now abandoned. --.

Column 1, before the "FIELD OF THE INVENTION", insert the following:

-- This is a continuation-in-part of application No. 07/930,443, filed on August 19, 1992, and a continuation-in-part of application No. 08/321,685, filed on October 12, 1994, now abandoned. Application No. 07/930,443, filed on August 19, 1992, is a continuation of application No. 07/524,263, filed May 16, 1990, now abandoned. --.

Signed and Sealed this

Twelfth Day of October, 2010

David J. Kappos
*Director of the United States Patent and Trademark Office*

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 2224 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 90..1472

(xi) SEQUENCE DESCRIPTION: SEQ ID NO: 1:

```
GCGAGCGCAG CGGAGCCTGG AGAGAAGGCG CTGGGCTGCG AGGGCGCGAG GGCGCGAGGG          60

CAGGGGGCAA CCGGACCCCG CCCGCACCC ATG GCG CCC GTC GCC GTC TGG GCC          113
                                Met Ala Pro Val Ala Val Trp Ala
                                 1               5

GCG CTG GCC GTC GGA CTG GAG CTC TGG GCT GCG GCG CAC GCC TTG CCC          161
Ala Leu Ala Val Gly Leu Glu Leu Trp Ala Ala Ala His Ala Leu Pro
         10                  15                  20

GCC CAG GTG GCA TTT ACA CCC TAC GCC CCG GAG CCC GGG AGC ACA TGC          209
Ala Gln Val Ala Phe Thr Pro Tyr Ala Pro Glu Pro Gly Ser Thr Cys
 25                  30                  35                  40

CGG CTC AGA GAA TAC TAT GAC CAG ACA GCT CAG ATG TGC TGC AGC AAA          257
Arg Leu Arg Glu Tyr Tyr Asp Gln Thr Ala Gln Met Cys Cys Ser Lys
                 45                  50                  55

TGC TCG CCG GGC CAA CAT GCA AAA GTC TTC TGT ACC AAG ACC TCG GAC          305
Cys Ser Pro Gly Gln His Ala Lys Val Phe Cys Thr Lys Thr Ser Asp
             60                  65                  70

ACC GTG TGT GAC TCC TGT GAG GAC AGC ACA TAC ACC CAG CTC TGG AAC          353
Thr Val Cys Asp Ser Cys Glu Asp Ser Thr Tyr Thr Gln Leu Trp Asn
         75                  80                  85

TGG GTT CCC GAG TGC TTG AGC TGT GGC TCC CGC TGT AGC TCT GAC CAG          401
Trp Val Pro Glu Cys Leu Ser Cys Gly Ser Arg Cys Ser Ser Asp Gln
     90                  95                 100

GTG GAA ACT CAA GCC TGC ACT CGG GAA CAG AAC CGC ATC TGC ACC TGC          449
Val Glu Thr Gln Ala Cys Thr Arg Glu Gln Asn Arg Ile Cys Thr Cys
105                 110                 115                 120

AGG CCC GGC TGG TAC TGC GCG CTG AGC AAG CAG GAG GGG TGC CGG CTG          497
Arg Pro Gly Trp Tyr Cys Ala Leu Ser Lys Gln Glu Gly Cys Arg Leu
                125                 130                 135

TGC GCG CCG CTG CGC AAG TGC CGC CCG GGC TTC GGC GTG GCC AGA CCA          545
Cys Ala Pro Leu Arg Lys Cys Arg Pro Gly Phe Gly Val Ala Arg Pro
            140                 145                 150

GGA ACT GAA ACA TCA GAC GTG GTG TGC AAG CCC TGT GCC CCG GGG ACG          593
Gly Thr Glu Thr Ser Asp Val Val Cys Lys Pro Cys Ala Pro Gly Thr
        155                 160                 165

TTC TCC AAC ACG ACT TCA TCC ACG GAT ATT TGC AGG CCC CAC CAG ATC          641
Phe Ser Asn Thr Thr Ser Ser Thr Asp Ile Cys Arg Pro His Gln Ile
    170                 175                 180

TGT AAC GTG GTG GCC ATC CCT GGG AAT GCA AGC ATG GAT GCA GTC TGC          689
Cys Asn Val Val Ala Ile Pro Gly Asn Ala Ser Met Asp Ala Val Cys
185                 190                 195                 200

ACG TCC ACG TCC CCC ACC CGG AGT ATG GCC CCA GGG GCA GTA CAC TTA          737
```

```
Thr Ser Thr Ser Pro Thr Arg Ser Met Ala Pro Gly Ala Val His Leu
            205                 210                 215

CCC CAG CCA GTG TCC ACA CGA TCC CAA CAC ACG CAG CCA ACT CCA GAA      785
Pro Gln Pro Val Ser Thr Arg Ser Gln His Thr Gln Pro Thr Pro Glu
            220                 225                 230

CCC AGC ACT GCT CCA AGC ACC TCC TTC CTG CTC CCA ATG GGC CCC AGC      833
Pro Ser Thr Ala Pro Ser Thr Ser Phe Leu Leu Pro Met Gly Pro Ser
            235                 240                 245

CCC CCA GCT GAA GGG AGC ACT GGC GAC TTC GCT CTT CCA GTT GGA CTG      881
Pro Pro Ala Glu Gly Ser Thr Gly Asp Phe Ala Leu Pro Val Gly Leu
            250                 255                 260

ATT GTG GGT GTG ACA GCC TTG GGT CTA CTA ATA ATA GGA GTG GTG AAC      929
Ile Val Gly Val Thr Ala Leu Gly Leu Leu Ile Ile Gly Val Val Asn
265                 270                 275                 280

TGT GTC ATC ATG ACC CAG GTG AAA AAG AAG CCC TTG TGC CTG CAG AGA      977
Cys Val Ile Met Thr Gln Val Lys Lys Lys Pro Leu Cys Leu Gln Arg
                285                 290                 295

GAA GCC AAG GTG CCT CAC TTG CCT GCC GAT AAG GCC CGG GGT ACA CAG     1025
Glu Ala Lys Val Pro His Leu Pro Ala Asp Lys Ala Arg Gly Thr Gln
            300                 305                 310

GGC CCC GAG CAG CAG CAC CTG CTG ATC ACA GCG CCG AGC TCC AGC AGC     1073
Gly Pro Glu Gln Gln His Leu Leu Ile Thr Ala Pro Ser Ser Ser Ser
            315                 320                 325

AGC TCC CTG GAG AGC TCG GCC AGT GCG TTG GAC AGA AGG GCG CCC ACT     1121
Ser Ser Leu Glu Ser Ser Ala Ser Ala Leu Asp Arg Arg Ala Pro Thr
            330                 335                 340

CGG AAC CAG CCA CAG GCA CCA GGC GTG GAG GCC AGT GGG GCC GGG GAG     1169
Arg Asn Gln Pro Gln Ala Pro Gly Val Glu Ala Ser Gly Ala Gly Glu
345                 350                 355                 360

GCC CGG GCC AGC ACC GGG AGC TCA GAT TCT TCC CCT GGT GGC CAT GGG     1217
Ala Arg Ala Ser Thr Gly Ser Ser Asp Ser Ser Pro Gly Gly His Gly
            365                 370                 375

ACC CAG GTC AAT GTC ACC TGC ATC GTG AAC GTC TGT AGC AGC TCT GAC     1265
Thr Gln Val Asn Val Thr Cys Ile Val Asn Val Cys Ser Ser Ser Asp
            380                 385                 390

CAC AGC TCA CAG TGC TCC TCC CAA GCC AGC TCC ACA ATG GGA GAC ACA     1313
His Ser Ser Gln Cys Ser Ser Gln Ala Ser Ser Thr Met Gly Asp Thr
            395                 400                 405

GAT TCC AGC CCC TCG GAG TCC CCG AAG GAC GAG CAG GTC CCC TTC TCC     1361
Asp Ser Ser Pro Ser Glu Ser Pro Lys Asp Glu Gln Val Pro Phe Ser
            410                 415                 420

AAG GAG GAA TGT GCC TTT CGG TCA CAG CTG GAG ACG CCA GAG ACC CTG     1409
Lys Glu Glu Cys Ala Phe Arg Ser Gln Leu Glu Thr Pro Glu Thr Leu
425                 430                 435                 440

CTG GGG AGC ACC GAA GAG AAG CCC CTG CCC CTT GGA GTG CCT GAT GCT     1457
Leu Gly Ser Thr Glu Glu Lys Pro Leu Pro Leu Gly Val Pro Asp Ala
            445                 450                 455

GGG ATG AAG CCC AGT TAACCAGGCC GGTGTGGGCT GTGTCGTAGC CAAGGTGGGC     1512
Gly Met Lys Pro Ser
            460

TGAGCCCTGG CAGGATGACC CTGCGAAGGG GCCCTGGTCC TTCCAGGCCC CCACCACTAG   1572

GACTCTGAGG CTCTTTCTGG GCCAAGTTCC TCTAGTGCCC TCCACAGCCG CAGCCTCCCT   1632

CTGACCTGCA GGCCAAGAGC AGAGGCAGCG AGTTGGGGAA AGCCTCTGCT GCCATGGTGT   1692

GTCCCTCTCG GAAGGCTGGC TGGGCATGGA CGTTCGGGGC ATGCTGGGGC AAGTCCCTGA   1752

CTCTCTGTGA CCTGCCCCGC CCAGCTGCAC CTGCCAGCCT GGCTTCTGGA GCCCTTGGGT   1812

TTTTTGTTTG TTTGTTTGTT TGTTTGTTTG TTTCTCCCCC TGGGCTCTGC CCAGCTCTGG   1872
```

```
CTTCCAGAAA ACCCCAGCAT CCTTTTCTGC AGAGGGGCTT TCTGGAGAGG AGGGATGCTG    1932

CCTGAGTCAC CCATGAAGAC AGGACAGTGC TTCAGCCTGA GGCTGAGACT GCGGGATGGT    1992

CCTGGGGCTC TGTGTAGGGA GGAGGTGGCA GCCCTGTAGG GAACGGGGTC CTTCAAGTTA    2052

GCTCAGGAGG CTTGGAAAGC ATCACCTCAG GCCAGGTGCA GTGGCTCACG CCTATGATCC    2112

CAGCACTTTG GGAGGCTGAG GCGGGTGGAT CACCTGAGGT TAGGAGTTCG AGACCAGCCT    2172

GGCCAACATG GTAAAACCCC ATCTCTACTA AAAATACAGA AATTAGCCGG GC            2224
```

(2) INFORMATION FOR SEQ ID NO: 2:

(i) SEQUENCE CHARACTERISTICS:
        (A) LENGTH: 461 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Pro Val Ala Val Trp Ala Ala Leu Ala Val Gly Leu Glu Leu
 1               5                  10                  15

Trp Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
            195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
    275                 280                 285

Lys Lys Pro Leu Cys Leu Gln Arg Glu Ala Lys Val Pro His Leu Pro
```

-continued

```
                290                 295                 300
Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
                340                 345                 350

Val Glu Ala Ser Gly Ala Gly Glu Ala Arg Ala Ser Thr Gly Ser Ser
                355                 360                 365

Asp Ser Ser Pro Gly Gly His Gly Thr Gln Val Asn Val Thr Cys Ile
                370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Cys Ala Phe Arg Ser
                420                 425                 430

Gln Leu Glu Thr Pro Glu Thr Leu Leu Gly Ser Thr Glu Glu Lys Pro
                435                 440                 445

Leu Pro Leu Gly Val Pro Asp Ala Gly Met Lys Pro Ser
450                 455                 460

(2) INFORMATION FOR SEQ ID NO: 3:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Val Cys Pro Gln Gly Lys Tyr Ile His Pro Gln Asn Asn Ser Ile Cys
1               5                   10                  15

Cys Thr Lys Cys His Lys Gly Thr Tyr Leu Tyr Asn Asp Cys Pro Gly
                20                  25                  30

Pro Gly Gln Asp Thr Asp Cys Arg Glu Cys Glu Ser Gly Ser Phe Thr
                35                  40                  45

Ala Ser Glu Asn His Leu Arg His Cys Leu Ser Cys Ser Lys Cys Arg
                50                  55                  60

Lys Glu Met Gly Gln Val Glu Ile Ser Ser Cys Thr Val Asp Arg Asp
65                  70                  75                  80

Thr Val Cys Gly Cys Arg Lys Asn Gln Tyr Arg His Tyr Trp Ser Glu
                85                  90                  95

Asn Leu Phe Gln Cys Phe Asn Cys Ser Leu Cys Leu Asn Gly Thr Val
                100                 105                 110

His Leu Ser Cys Gln Glu Lys Gln Asn Thr Val Cys Thr Cys His Ala
                115                 120                 125

Gly Phe Phe Leu Arg Glu Asn Glu Cys Val Ser Cys Ser Asn Cys Lys
                130                 135                 140

Lys Ser Leu Glu Cys Thr Lys Leu Cys
145                 150

(2) INFORMATION FOR SEQ ID NO: 4:

(i) SEQUENCE CHARACTERISTICS:
```

(A) LENGTH: 163 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 4:

```
Thr Cys Arg Leu Arg Glu Tyr Tyr Asp Gln Thr Ala Gln Met Cys Cys
1               5                  10                  15

Ser Lys Cys Ser Pro Gly Gln His Ala Lys Val Phe Cys Thr Lys Thr
            20                  25                  30

Ser Asp Thr Val Cys Asp Ser Cys Glu Asp Ser Thr Tyr Thr Gln Leu
        35                  40                  45

Trp Asn Trp Val Pro Glu Cys Leu Ser Cys Gly Ser Arg Cys Ser Asp
    50                  55                  60

Asp Gln Val Glu Thr Gln Ala Cys Thr Arg Glu Gln Asn Arg Ile Cys
65                  70                  75                  80

Thr Cys Arg Pro Gly Trp Tyr Cys Ala Leu Ser Lys Gln Glu Gly Cys
                85                  90                  95

Arg Leu Cys Ala Pro Leu Arg Lys Cys Arg Pro Gly Phe Gly Val Ala
            100                 105                 110

Arg Pro Gly Thr Glu Thr Ser Asp Val Val Cys Lys Pro Cys Ala Pro
        115                 120                 125

Gly Thr Phe Ser Asn Thr Thr Ser Ser Thr Asp Ile Cys Arg Pro His
    130                 135                 140

Gln Ile Cys Asn Val Val Ala Ile Pro Gly Asn Ala Ser Met Asp Ala
145                 150                 155                 160

Val Cys Thr
```

(2) INFORMATION FOR SEQ ID NO: 5:

(i) SEQUENCE CHARACTERISTICS:
          (A) LENGTH: 119 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 5:

```
Gln Asn Leu Glu Gly Leu His His Asp Gly Gln Phe Cys His Lys Pro
1               5                  10                  15

Cys Pro Pro Gly Glu Arg Lys Ala Arg Asp Cys Thr Val Asn Gly Asp
            20                  25                  30

Glu Pro Asp Cys Val Pro Cys Gln Glu Gly Lys Glu Tyr Thr Asp Lys
        35                  40                  45

Ala His Phe Ser Ser Lys Cys Arg Arg Cys Arg Leu Cys Asp Glu Gly
    50                  55                  60

His Gly Leu Glu Val Glu Ile Asn Cys Thr Arg Thr Gln Asn Thr Lys
65                  70                  75                  80

Cys Arg Cys Lys Pro Asn Phe Phe Cys Asn Ser Thr Val Cys Glu His
                85                  90                  95

Cys Asp Pro Cys Thr Lys Cys Glu His Gly Ile Ile Lys Glu Cys Thr
            100                 105                 110

Leu Thr Ser Asn Thr Lys Cys
        115
```

(2) INFORMATION FOR SEQ ID NO: 6:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Ala Cys Pro Thr Gly Leu Tyr Thr His Ser Gly Glu Cys Cys Lys Ala
1               5                   10                  15

Cys Asn Leu Gly Glu Gly Val Ala Gln Pro Cys Gly Ala Asn Gln Thr
            20                  25                  30

Val Cys Glu Pro Cys Leu Asp Ser Val Thr Ser Ser Asp Val Val Ser
        35                  40                  45

Ala Thr Glu Pro Cys Lys Pro Cys Thr Glu Cys Val Gly Leu Gln Ser
    50                  55                  60

His Ser Ala Pro Cys Val Glu Ala Asp Asp Ala Val Cys Arg Cys Ala
65                  70                  75                  80

Tyr Gly Tyr Tyr Gln Asp Glu Thr Thr Gly Arg Cys Glu Ala Cys Arg
                85                  90                  95

Val Cys Glu Ala Gly Ser Gly Leu Val Phe Ser Cys Gln Asp Lys Gln
            100                 105                 110

Asn Thr Val Cys Glu Glu Cys Pro Asp Gly Thr Tyr Ser Asp Glu Ala
            115                 120                 125

Asn His Val Asp Pro Cys Leu Pro Cys Thr Val Cys Glu Asp Thr Glu
            130                 135                 140

Arg Gln Leu Arg Glu Cys Thr Arg Trp Ala Asp Ala Glu Cys Glu
145                 150                 155
```

(2) INFORMATION FOR SEQ ID NO: 7:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Ala Cys Arg Glu Lys Gln Tyr Leu Ile Asn Ser Gln Cys Cys Ser Leu
1               5                   10                  15

Cys Gln Pro Gly Gln Lys Leu Val Ser Asp Cys Thr Glu Phe Thr Glu
            20                  25                  30

Thr Glu Cys Leu Pro Cys Gly Glu Ser Glu Phe Leu Asp Thr Trp Asn
            35                  40                  45

Arg Glu Thr His Cys His Gln His Lys Tyr Cys Asp Pro Asn Leu Gly
    50                  55                  60

Leu Arg Val Gln Gln Lys Gly Thr Ser Glu Thr Asp Thr Ile Cys Thr
65                  70                  75                  80

Cys Glu Glu Gly Trp His Cys Thr Ser Glu Ala Cys Glu Ser Cys Val
                85                  90                  95

Leu His Arg Ser Cys Ser Pro Gly Phe Gly Val Lys Gln Ile Ala Thr
            100                 105                 110

Gly Val Ser Asp Thr Ile Cys Glu Pro Cys Pro Val Gly Phe Phe Ser
            115                 120                 125
```

-continued

```
Asn Val Ser Ser Ala Phe Glu Lys Cys His Pro Thr Ser Cys Glu Thr
    130                 135                 140

Lys Asp Leu Val Val Gln Gln Ala Gly Thr Asn Lys Thr Asp Val Val
145                 150                 155                 160

Cys Gly
```

(2) INFORMATION FOR SEQ ID NO: 8:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Asn Cys Val Lys Asp Thr Tyr Pro Ser Gly His Lys Cys Cys Arg Glu
1               5                   10                  15

Cys Gln Pro Gly His Gly Met Val Ser Arg Cys Asp His Thr Arg Asp
            20                  25                  30

Thr Val Cys His Pro Cys Glu Pro Gly Phe Tyr Asn Glu Ala Val Asn
            35                  40                  45

Tyr Asp Thr Cys Lys Gln Cys Thr Gln Cys Asn His Arg Ser Gly Ser
    50                  55                  60

Glu Leu Lys Gln Asn Cys Thr Pro Thr Glu Asp Thr Val Cys Gln Cys
65                  70                  75                  80

Arg Pro Gly Thr Gln Pro Arg Gln Asp Ser Ser His Lys Leu Gly Val
            85                  90                  95

Asp Cys Val Pro Cys Pro Pro Gly His Phe Ser Pro Gly Ser Asn Gln
            100                 105                 110

Ala Cys Lys Pro Trp Thr Asn Cys Thr Leu Ser Gly Lys Gln Ile Arg
            115                 120                 125

His Pro Ala Ser Asn Ser Leu Asp Thr Val Cys Glu
    130                 135                 140
```